(12) United States Patent
Aouad (10) Patent No.: US 10,161,946 B2
(45) Date of Patent: Dec. 25, 2018

(54) APPARATUS AND METHOD FOR DEVELOPING FORMULATIONS

(71) Applicant: Salah M. Aouad, Casablanca (MA)

(72) Inventor: Salah M. Aouad, Casablanca (MA)

(*) Notice: Subject to any disclaimer, the term of this patent is extended or adjusted under 35 U.S.C. 154(b) by 105 days.

(21) Appl. No.: 15/227,882

(22) Filed: Aug. 3, 2016

(65) Prior Publication Data

US 2017/0016926 A1 Jan. 19, 2017

Related U.S. Application Data

(63) Continuation of application No. 14/841,336, filed on Aug. 31, 2015, now abandoned, which is a
(Continued)

(51) Int. Cl.
*G01N 35/00* (2006.01)
*B01F 1/00* (2006.01)
(Continued)

(52) U.S. Cl.
CPC ..... *G01N 35/00584* (2013.01); *B01F 1/0038* (2013.01); *B01F 13/1055* (2013.01); *B01F 13/1066* (2013.01); *B01F 15/00032* (2013.01); *B01F 15/00064* (2013.01); *B01F 15/00194* (2013.01); *B01F 15/0425* (2013.01); *B01F 15/0445* (2013.01); *B01F 15/065* (2013.01);
(Continued)

(58) Field of Classification Search
CPC .......... G01N 35/00584; G01N 35/025; G01N 35/1002; G01N 35/1065; G01N 35/0099; G01G 19/24; G01G 19/22; B01F 15/065; B01F 15/00194; B01F 15/0425; B01F 13/1055; B01F 15/00064; B01F 15/00032; B01F 1/0038; B01F 15/0441; B01F 2215/0032; B01F 2215/0037; B01F 2015/0221; B01F 2215/0014
See application file for complete search history.

(56) References Cited

U.S. PATENT DOCUMENTS 4,415,446 A  11/1983  Osborne
4,428,679 A   1/1984  Fischer et al.
(Continued)

FOREIGN PATENT DOCUMENTS

DE  10 2009 040514 A1  3/2011
JP        1 180229 A    7/1989
(Continued)

OTHER PUBLICATIONS

M. Legrand and P. Bolla, "A Fully Automatic Apparatus for Chemical Reactions on the Laboratory Scale", Journal of Automatic Chemistry, vol. 7, No. 1, pp. 31-37, (1985).
(Continued)

*Primary Examiner* — Jason K Niesz
(74) *Attorney, Agent, or Firm* — Winston & Strawn LLP (57) ABSTRACT

The various embodiments of the present invention generally relate to an automated apparatus, wherein the automated apparatus is configured to formulate a target entity, thereby developing formulations of the target entity by using a high throughput screening (HTS) procedure and method of employing the presented automated apparatus is also disclosed herein. Other advantages that are understood from the present disclosure will further be apparent to the reader.

20 Claims, 1 Drawing Sheet

Related U.S. Application Data continuation of application No. 13/426,261, filed on Mar. 21, 2012, now Pat. No. 9,138,693.

(60) Provisional application No. 61/466,340, filed on Mar. 22, 2011, provisional application No. 61/200,488, filed on Dec. 1, 2008.

(51) Int. Cl.
*B01F 13/10* (2006.01)
*B01F 15/00* (2006.01)
*G01G 19/24* (2006.01)
*B01F 15/06* (2006.01)
*G01N 35/02* (2006.01)
*G01N 35/10* (2006.01)
*B01F 15/04* (2006.01)
*G01G 19/22* (2006.01)
*B01F 15/02* (2006.01)

(52) U.S. Cl.
CPC ......... *G01G 19/24* (2013.01); *G01N 35/0099* (2013.01); *G01N 35/025* (2013.01); *G01N 35/1002* (2013.01); *G01N 35/1065* (2013.01); *B01F 15/0441* (2013.01); *B01F 2015/0221* (2013.01); *B01F 2215/0014* (2013.01); *B01F 2215/0032* (2013.01); *B01F 2215/0037* (2013.01); *G01G 19/22* (2013.01)

(56) References Cited

U.S. PATENT DOCUMENTS

| | | | |
|---|---|---|---|
| 4,469,146 A | 9/1984 | Campbell et al. |
| 4,476,999 A | 10/1984 | Bilbrey |
| 4,830,508 A | 5/1989 | Higuchi et al. |
| 4,964,185 A | 10/1990 | Lehn |
| 5,402,834 A | 4/1995 | Levin et al. |
| 5,607,651 A | 3/1997 | Thomas et al. |
| 5,632,960 A | 5/1997 | Ferri et al. |
| 5,720,154 A | 2/1998 | Lasher et al. |
| 5,833,364 A | 11/1998 | Rushing et al. |
| 5,874,049 A | 2/1999 | Ferri, Jr. et al. |
| 6,007,236 A | 12/1999 | Maguire |
| 6,061,608 A | 5/2000 | Moldavsky |
| 6,126,904 A | 10/2000 | Zuellig et al. |
| 6,224,252 B1 | 5/2001 | Munroe et al. |
| 6,357,906 B1 | 3/2002 | Baudoin et al. |
| 6,402,363 B1 | 6/2002 | Maguire |
| 6,605,256 B1 | 8/2003 | Guller et al. |
| 6,673,316 B1 | 1/2004 | Okamoto et al. |
| 6,764,212 B1 | 7/2004 | Nitta et al. |
| 6,827,478 B2 | 12/2004 | Becker et al. |
| 7,134,459 B2 | 11/2006 | Carlson et al. |
| 7,140,405 B2 | 11/2006 | Lewis et al. |
| 7,144,552 B1 | 12/2006 | Fukuizumi et al. |
| 7,222,753 B2 | 5/2007 | Hayduk |
| 7,361,309 B2 | 4/2008 | Vann et al. |
| 9,138,693 B2 | 9/2015 | Aouad |
| 2003/0142580 A1 | 7/2003 | Maguire |
| 2003/0185094 A1 | 10/2003 | Packard |
| 2005/0047964 A1 | 3/2005 | Nishida et al. |
| 2005/0235740 A1 | 10/2005 | Desie et al. |
| 2012/0241045 A1 | 9/2012 | Aouad |

FOREIGN PATENT DOCUMENTS

| | | |
|---|---|---|
| WO | WO 97/21528 A1 | 6/1997 |
| WO | WO2004/041202 A2 | 5/2004 |
| WO | WO2006/054964 A1 | 5/2006 |

OTHER PUBLICATIONS

Article: "Accelerator SLT100/106/112 Synthesizer," Chemspeed Technologies®, 6 pages (2006).

Chata article, "Chem+Mix™ Automated Solution Preparation System Cost-Effective, Efficient, Convenient—It's all in the Mix", The Science of Lab Efficiency, www.Chatasolutions.com, 4 pages (2006).

International Search Report & Written Opinion PCT/MA2012/000003, dated Jul. 18, 2012.

International Search Report PCT/MA2016/000013, dated Feb. 5, 2017.

APPARATUS AND METHOD FOR DEVELOPING FORMULATIONS

RELATED APPLICATION

The present application claims the benefit of U.S. Provisional Application No. 62/200,488, filed Aug. 3, 2015, which is expressly incorporated herein by reference in its entire for all purpose.

FIELD OF INVENTION

The invention generally relates to a computer automated apparatus that prepares, screens and classify large numbers of ingredient combinations (additives and excipients etc.) in order to formulate new entities including chemical or pharmaceutical compounds and food preparations using high throughput screening (HTS) and methods of serial preparation and screening of the said formulations using the disclosed apparatus.

BACKGROUND OF THE INVENTION

Formulation is a process through which chemical and natural entities e.g., natural or synthetic chemical compounds, polymers or nanostructures, biological molecules or molecular complexes, drugs/medicines, active pharmaceutical ingredients (APIs), nutrients, fragrances or combination thereof are prepared and combined with secondary materials (ingredients) such as excipients and additives.

This process is used in the studying and characterization of new discovered entities for their development into final products. This process is also necessary to ensure that the final products possesses optimal activity and safety to consumers (including humans) and that they are capable of long-term storage. In other cases, this process is mobilized by producers/manufacturers to receive approval, from local and/or international regulatory authorities, for the commercialization of a new entity or an alternative improved version of old entities or products.

Therefore, formulation is a critical step for preparing and manufacturing an entity or product because it affects the development, marketing and consumption of that entity. However, in industrial, as well as academic settings, finding the right formulation is oftentimes a complex, time-consuming and costly endeavor. This is due to the following challenges. First, there are too many criteria to meet in each formulation. A qualified formulation has to offer solubility, long-term stability, as well as other criteria such as permeability. All these criteria have to be met without compromising the activity and efficacy of the entity of interest and its safety for human consumption. Second, there are too many ingredients, conditions to be tested, and operations to consider for every single property, e.g., stability, in a given limited amount of time. Third, the whole process is very time-consuming because it is based on trial and error and all the operations are still carried out manually. All these challenges render current formulation processes slow, inaccurate, non-reproducible, and very often hazardous to the professional who performs the process because of their direct and repeated/prolonged exposure to chemicals. These problems generally translate into the high-cost and poor-outcome that are well known for the formulation processes.

As such, there remains a need for an apparatus and methods that can screen, search, and discover optimal formulation(s) in a rapid and robust way. Embodiments of the present invention provide a novel solution to the aforementioned problems. There are also other deficiencies that can be remedied based on illustrative descriptions provided herein.

SUMMARY OF THE INVENTION

In accordance with one embodiment of the present invention, an automated system for developing new formulations of a target entity is contemplated. The system may comprise an automated apparatus comprising a plurality of screening lines, a plurality of analytical devices, and an articulated robotic arm.

Each of the plurality of screening lines may comprise a plurality of upstream storage containers adapted to receive raw materials, wherein the raw materials comprise the target entity and secondary ingredients at least one device that is adapted to condition before they are received in the storage containers, while they are in the storage containers, or after they exit the storage containers; a dispensing system comprising a central common collector and a plurality of conduits connected to each of the storage containers; a dosing system that measures amounts of the target entity and the secondary ingredients to be combined as an ingredient combination; a collector that pools the target entity and the secondary ingredients as the ingredient combination; a plurality of formulation chambers adapted to prepare formulations from the ingredient combination and perform stress treatment on the prepared formulations; a plurality of in-line sensors installed in the formulation chambers for monitoring properties of the ingredient combination and screening formulations of the ingredient combination; a plurality of actuators comprising pumps, valves, nozzles, and stirrers adapted to transfer raw materials and formulation between compartments and chambers; at least one injector that is adapted to administer additional target entity and secondary ingredients into one of the formulation chambers to be formulated with the ingredient combination in that formulation chamber; an auto-sampler for drawing out a portion of formulations prepared by the formulation chambers as samples or final formulated materials; at least one carousel for holding a plurality of vessels for containing the drawn samples or final formulated materials; and a waste line for evacuating waste out of the apparatus after a cleaning cycle.

The plurality of analytical devices may be coupled to the apparatus that are controlled by a computer and the articulated robotic arm may be connected to the apparatus and operated by the computer for automatically loading and unloading the formulation chambers and vessels between the apparatus and the analytical devices for analyses.

In one variant, the plurality of screening lines may comprise 5 to 50 screening lines that are adapted to conduct high throughput screening or ultrahigh throughput screening of ingredients and formulations.

In one variant, the apparatus may be adapted to handle a chemical or a biological molecule including a nucleic acid, protein, antibody, peptide, pharmaceutical, biological drug, medicine, diagnostic reagent, cosmetic, nutrient, chemical reagent, polymer, nanostructure or a combination thereof.

In one variant, the apparatus may be adapted to handle a pharmaceutical, a chemical or a food ingredient including liquids, solvents, solids, vehicles, oils, buffers, solubilizers, surfactants, stabilizers, antimicrobials, preservatives, sweeteners, flavors, dyes, additives, excipients or a combination thereof.

In one variant, the apparatus may be adapted to categorize the raw materials in storage containers as separate libraries, wherein one or more libraries are dedicated to target entities and multiple libraries are dedicated to secondary ingredients.

In one variant, one of the prepared formulations may be cold or radioactive solution, a chemical or biological medicine, a diagnostic reagent, a cosmetic/fragrance, an agrochemical, a coating solution, a food recipe or a processed food preparation or a combination thereof.

In one variant, the conditioning of raw materials may comprise degassing, heating, cooling or making a gradient of materials or a combination thereof.

In one variant, the central common collector may be adapted to perform high speed parallel dispensing and the plurality of conduits may be flexible conduits configured to perform high precision dispensing and dosing.

In one variant, the dosing system may comprise a mechanism configured to measure weight of the target entity and secondary ingredients and a mechanism configured to measure flow rate of the target entity and secondary ingredients. The mechanism configured to measure weight of the target entity and secondary ingredients may comprise load cells installed on the storage containers.

In one variant, the plurality of actuators may further comprise heating and cooling devices, homogenizers, UV and visible light sources or a combination of thereof that are configured to process the raw materials, adjust formulations, and introduce acute stress into formulations.

In one variant, the plurality of sensors may comprise a thermometer, a volume detector, a pH-meter, a nephelometer, a viscosimeter, a particle counter, a camera or a combination thereof.

In one variant, the analytical devices may comprise at least a plate reader, a HPLC, a LC/MS, a NMR, a SPR/Biacore, or a combination thereof that is used to complement the monitoring and screening activities of the in-line sensors.

In one variant, the formulation chambers may include single multi-FC and multi-SC plates that may be loaded or unloaded from the apparatus manually or automatically using the robotic arm for long term external incubations followed by reloading to the apparatus or for disposal and replacement by new unpacked sterile plates.

In accordance with another embodiment of the present invention, a method for developing new formulations of a target entity is contemplated. The method may comprise receiving the target entity to be formulated; conditioning the received target entity; combining the target entity with secondary ingredients to produce an ingredient combination; formulating the ingredient combination to produce formulations; subjecting the formulations to a stress treatment; screening the formulations for the target entity's physical, chemical and functional properties; delivering a portion of the formulations as samples or final formulations to a plurality of vessels; and analyzing and comparing screening data from screening lines for finding hit formulations.

In one variant, the preparation of ingredient combination may be based on a mechanism of high speed combinatorial formulation consisting in preparing multiple separate ingredient combinations at once in a short time, through the simultaneous execution of parallel ingredient dispensing in each screening line and differential ingredient dispensing between different screening lines.

In one variant, the step of screening may comprise at least three screening types, and the at least three screening types may comprise formulation screening involving in-line monitoring of the target entity's properties, stability screening involving in-line and tandem monitoring of the target entity's alteration under stress, and functional screening involving off-line monitoring of the target entity's functional activities.

In one variant, the stress treatment may comprise chemical stress, physical stress or a combination thereof that can be executed in-line in stress chambers for short term forced stability studies and be performed outside the apparatus for long term stability studies.

In one variant, the step of analyzing and comparing may comprise comparing all produced formulations utilizing a computer and a plurality of analytic devices.

In accordance with yet another embodiment of the present invention, a computer configured to operate an automated system for developing new formulations of a target entity comprising an automated apparatus, a plurality of analytic devices, and an articulated robotic arm is contemplated. The computer may comprise a processor, a non-transient memory coupled to the processor, and a set of computer instructions contained in the non-transient memory that are executable by the processor. The set of computer instructions, when executed by the processor, may cause the processor to instruct the automated system to perform the steps of conditioning the target entity and secondary ingredients received in the apparatus; dispensing the target entity and secondary ingredients through a dispensing system of the apparatus comprising a central common collector and a plurality of conduits, the target entity and secondary ingredients are dispensed to the central common collector via the plurality of conduits; measuring amounts of the target entity and the secondary ingredient to be combined as an ingredient combination; pooling the target entity and the secondary ingredients as the ingredient combination; preparing formulations from the ingredient combination and performing stress treatment in a plurality of formulation chambers of the apparatus; monitoring properties of the ingredient combination and screening formulations of the ingredient combination through a plurality of in-line sensors installed in the formulation chambers; transferring the target entity and the secondary ingredients between compartments and chambers of the apparatus via a plurality of actuators comprising pumps, valves, nozzles, and stirrers; administering additional target entity and secondary ingredients into one of the formulation chambers to be formulated with the ingredient combination in that formulation chamber from an injector; drawing out a portion of formulations prepared by the formulation chambers as samples or final formulated materials to a carousel for holding a plurality of vessels for containing the drawn samples or final formulated materials; instructing the analytical devices to screen the prepared formulations and find hit formulations; and operating the robotic arm to load and unload the formulation chambers and vessels between the apparatus and the analytics devices for analysis.

BRIEF DESCRIPTION OF THE FIGURES

The nature and various advantages of the present invention will become more apparent upon consideration of the following detailed description, taken in conjunction with the accompanying drawings, in which like reference characters refer to like parts throughout, and in which.

DETAILED DESCRIPTION OF THE INVENTION

Below are the definitions and meanings of key and regularly used terminologies:

a) "Raw materials" refer to initial ingredients of a formulation that are still in the stored status before their entry to the formulation and screening process. Raw materials comprise two major categories of ingredients, target entities and secondary ingredients.

b) "Target entity" refers to a material that may be prepared, formulated, and then checked by this technology for the effect of several formulations on its chemical and physical properties as well as functional activity. Target entity may be a chemical compound or complex of compounds consisting in an experimental or established drug/medicine, API or a pesticide, herbicide or insecticide and the like. It may also be an experimental or industrial chemical reagent, polymer, a nanostructure or a manufacturing intermediate. On the other hand, target entity may be a natural, organic biological molecule or complex of molecules (e.g. a peptide, a natural protein, a recombinant or fusion protein (chimera) or protein complex, an antibody, a hormone or a nucleic acid DNA or RNA entity) or combinations thereof. Other examples of target entity may be a crude or purified animal or plant extract (including medicinal) or processed foods and nutrient.

c) "Secondary ingredients" refers to the materials that will be tested by this technology for their capacity to protect, preserve or improve and extend target entity functional, chemical and physical properties (e.g., excipients, additives, preservatives or the like). Secondary agents also refer to reagents that may be combined with the raw materials in order to reveal (to detectors 60, 72, 86) whether target properties (chemical, physical or functional) of the target entity have been met in one or more screened formulations. This type of secondary ingredients can be a fluorescent or radio-labeled substrate or ligand of the target entity or just any revelation/detection dye or molecular probe known in the art of signal detection.

d) "Ingredient combination" refers to a mix of dry powder/solid state ingredients combining the target entity with one or more secondary ingredients.

e) "Ingredient premix" refers to the aqueous/liquid version of "ingredient combination" after combination of target entity and secondary ingredients was suspended in water or relevant solvent. It is an early, and often crude non homogenous, version of the final formulation. It generally lies between the collector 46 and PC 54.

f) "Formulation" it is a liquid solution, a preparation, a suspension, a slurry or a colloid referring to a more advanced or final version of the ingredient premix. It is generally formed in FC 66 and is the target of testing and screening operations performed by the proposed apparatus. The term "Formulation" is also used to name the act of preparation of a chemical, pharmaceutical or a food preparation.

An illustrative apparatus for developing new formulations using high throughput screening is described. The apparatus involves screening for, searching and detecting optimal formulation(s) of a target entity or product. This apparatus possesses a large storage capacity (multiplicity of ingredients), a robust mechanism of combinatorial formulation and parallel processing, a high throughput capability of formulation and screening as well as a sophisticated program of analyzing, organizing and reporting screening outcomes. These capabilities allow the apparatus to prepare automatically a large number of ingredient combinations, formulate them, test them simultaneously and then to classify them according to performance. Therefore, a user simply places an order on a computer, selects a target entity to formulate and then comes back to recover the right formulation(s) of selected target entity.

The automation and integration of these operations into one single apparatus provides several advantages such as widening screening scope, shortening screening time, increasing screening productivity and hit rate, developing formulations with high precision and fidelity, providing a large formulation capacity and throughput, complying with applicable regulations and quality standards (e.g., GLP, GMP, GCP etc.) and other advantages. Furthermore, this apparatus renders the formulation process completely labor free, which saves time and assures advanced safety to users, because it eliminates their exposure to all kinds of chemical, biological and physical hazards. Such apparatus also addresses other challenges encountered by existing conventional formulation procedures and techniques. The apparatus has applications in academic, industrial setting (pharmaceutical, chemical and food industries) as well as in healthcare and in regulatory sectors. Academic users of the apparatus may be universities, research laboratories and other institutions. In pharmaceutical industry, the users of the apparatus may be pharmaceutical and biotech companies, generic drug manufacturers, contract research organizations (CROs), life sciences & diagnostic suppliers and cosmetics companies. In the pharmaceutical industry, for instance, the apparatus may be used during R&D such as drug discovery and development. Uses in drug discovery may include lead optimization, which may comprise characterization of hits, (e.g., solubility, stability, drug testing and confirmation in vitro in cell-lines); optimization of leads and/or comparison between structural analogs. Uses in drug development may include pre-clinical trials, which comprises testing of drug candidates in vivo animal studies (e.g., toxicity, maximum tolerated dose (MTD), efficacy, pharmacokinetic/pharmacodynamic (PK/PD) and absorption, distribution, metabolism, excretion and toxicity (ADMET), bioavailability (BA) studies; and/or formulating new chemical entities (NCE's) for manufacturing of first batches required for the entry to clinical phase I. Uses in drug development may also include optimizing of final drug versions before phase IV clinical studies and market launch.

The apparatus has applications even after drug commercialization, during post-marketing phase. These applications may include but not limited to formulation of generic and follow-on/biosimilar versions of established branded chemical or biological drugs; preparation of modified or personalized drug formulations by compounding pharmacies and hospitals, as well as re-formulation and/or optimization of old existing branded or generic drugs. Alternatively, the apparatus can be mobilized in the discovery and development of secondary ingredients e.g., new additives, excipients, and stabilizers or in the development and optimization of consumption products (e.g., improvement of color, glossiness, aroma, flavors, texture, consistence, strength and adhesion of food products).

In chemical industry, the users of the apparatus may be entities that manufacture paints, polymers, construction fluids, coatings (including but not limited to industrial coatings, textile, electronic circuits and IT), pesticides, fertilizers and chemical reagents.

In food industry, the users of the apparatus may be food manufacturers of diaries, ice-creams, soups, drinks, juices etc., hospitality (restaurant and hotels), catering providers and domestic households are other user of the food sector.

Figure 1:
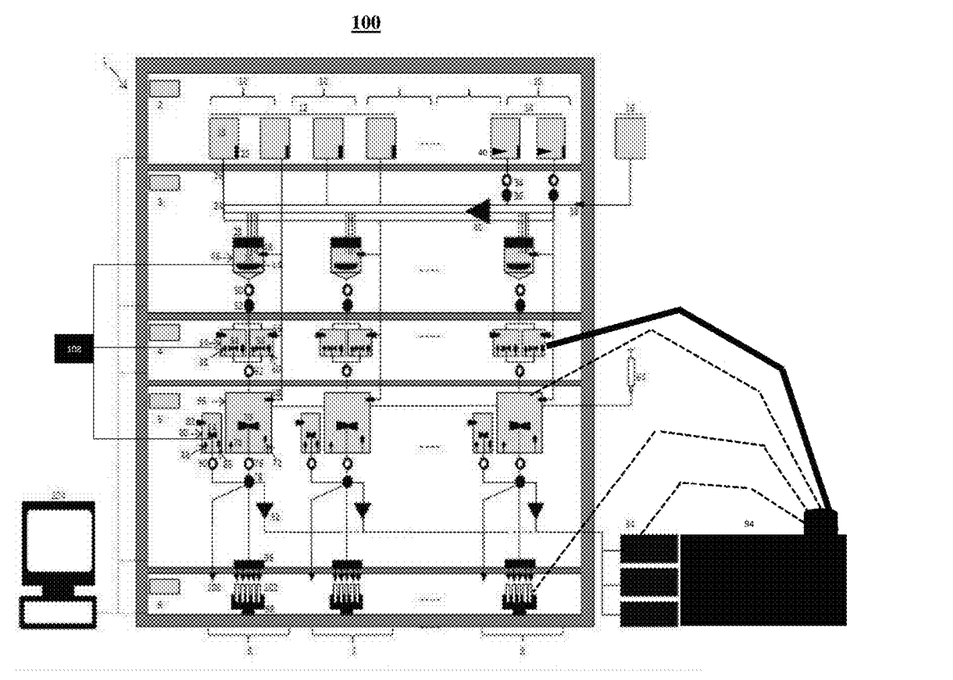
FIG. 1 shows an illustrative system for developing new formulations using high throughput screening in accordance with some embodiments of the present invention.

FIG. 1 shows an illustrative system 100 for developing new formulations using high throughput screening in accordance with some embodiments of the present invention. The system 100 may comprise a formulation preparation and screening apparatus 1, a station composed of one or more external devices 94 and a robotic arm coupled to the apparatus 1 and a computer 104 electrically connected to the apparatus 1 and the devices 94. The computer 104 includes a processor and is configured with software, data, and/or peripherals that control the operation of the apparatus 1 and/or the devices 94. Controlling the operation of the apparatus 1 includes controlling various actuators e.g., pumps, valves, lamps, stirrers as well as sensors/probes/detectors and recording the data generated from the sensors/probes and detectors. The computer 104 also includes a non-transient memory and/or transient memory in which the software and data are stored. Software and data are processed by the processor to generate instructions that prompt the apparatus 1, the devices 94, and other components of the system 100 may have to perform the steps described in this disclosure.

Depending on the setting, apparatus 1 may comprise two or more series of material formulation and screening, called screening lines 8. In busy and wealthy industrial settings, with highly populated R&D pipelines, apparatus 1 may be composed of several dozens, i.e., exceeding fifty or up to a hundred, screening lines 8. Each screening line 8 may be composed of five compartments 2, 3, 4, 5, and 6 that may be set vertically in the following order, compartment 2 on the top and compartment 6 at the bottom. Each compartment is specialized in an operation or group of operations as follows: compartment 2 for storage, compartment 3 for dispensing and dosing, compartment 4 for pre-formulation, compartment 5 for formulation, stress and monitoring/screening, and compartment 6 for discharge and delivery of formulations and waste-line. Therefore, compartments in each screening line 8 are configured to either store, dose, formulate or test raw materials. Depending on the throughput of the apparatus 1 (i.e., number of stored raw materials and screening lines) compartment 2 may be common to, and thus used by, all downstream screening lines or rather individualized (one storage compartment for each screening line 8). The compartments of each screening line may be isolated from each other without interrupting the flow communication between the compartments 2, 3, 4, 5, 6. Consequently, each screening line 8 may comprise a plurality of containers 18 for holding raw materials; one or more devices 40 adapted for the conditioning of raw materials; a dispensing system adapted to selectively dispense raw materials (target entity and secondary ingredients); a dosing system 30, 44 adapted to dose raw materials to be used in a formulation; a collector 46 for pooling raw materials into an ingredient combination; an active transfer mechanism that includes nozzles 48 adapted to suspend and transfer the ingredient combinations to the downstream compartments 4, 5; a plurality of formulation chambers (PCs 54, FC 66, SC 80) each one specialized for a formulation type and/or a stress treatment; and finally a mechanism 96, 98 for discharging of formulations out of apparatus 1 into appropriate independent vessels 102; and a waste-line 100. Each screening line 8 may also include a plurality of sensors 20, 44, 60, 72, 86 scattered and associated with several components of the screening line 8 including formulation chambers (PCs 54, FC 66 SC 80), and a plurality of actuators mobilized in the conditioning; the transport between compartments, the formulation and the stress of either of raw materials, ingredient combinations or final formulations.

Compartment 2 is the compartment that may allow apparatus 1 to store limited selection or large numbers of raw materials for ready processing and formulation. The storage compartment 2 may comprise a plurality of containers 18 for holding raw materials. The containers 18 may be canisters, plug-and-use cartridges, cans, bottles or other structures that are configured to hold solid (12) or liquid (14) raw materials except gas. The storage throughput can be preferably high, and may consist in a hundred or hundreds of small, to very small, containers 18, with 100 g ingredient capacity or less for each container 18. Otherwise, containers 18 throughput can be limited to a dozen or dozens of containers 18 with much higher capacity starting by 5 Kg ingredient capacity. The containers 18 can preferably be cylindrical, but can also be cubic, hexagonal, square, rectangular or any other shape that can be arrayed in a regular pattern while allowing access for replacing them or their contents. The containers 18 are arranged in a manner such that they could be operatively associated with the dispensing mechanism (described below). Additionally, Apparatus 1 may be connected via an inlet 38 to one or more external raw materials sources 16 consisting in either large containers like gas tanks and/or, transient containers storing fresh preparations, single use ingredients or perishable materials etc. But optionally, the containers 16 may also be included in the storage compartment 2. The containers 16 are also arranged in a manner such that they could be operatively associated with the dispensing mechanism (described below). Depending on the form of the raw material, the target entities and the secondary ingredients are placed in the appropriate containers.

The containers 18 may be organized into sections called libraries 10 (or categories 10). The libraries 10 may include libraries 10 for storing target entities and libraries 10 for storing secondary ingredients.

In the pharmaceutical industry for instance, the containers 18 may be arranged to form one or more libraries for target compounds (e.g., HTS hits, drug candidates or some structural analogs) and several libraries for secondary ingredients, e.g., a library of solvents, a library of buffers, a library of solubilizers, and a library of antimicrobials, a library of stabilizers, etc. Each library 10 may include one or more containers 18. The containers 18 may also be grouped based on the form of raw materials. For example, group 12 of containers may be dedicated to the storage of solid form ingredients and group 14 of containers to the storage of liquid solvents. The containers 16 may also be organized to be part of a library or to have their libraries whether they are outside the apparatus 1 or included in the storage compartment 2.

One or several containers 18, 12 and 14 may comprise a heating actuator (e.g., resistance or heating coil) 40 configured to heat one or several raw materials and form a fast and ready-to-use source of hot materials that can be immediately formulated in downstream compartment 3 in the collector 46. The containers 18, 16 may also be connected to load cells 20 configured to dose material exits from the containers 18, 16. As such, it is preferable that the load cells 20 are installed at the bottom of the containers 18, 16 or at the output or near the output of the containers 18, 16 where raw material exits.

The dispensing system is the structure that may allow each screening line 8 to release desired raw materials from their storage sources and convey them to downstream compartments for further processing and screening. The dispensing system may consist in a steady/stationary non-moving structure composed of a plurality of flexible dispensing conduits 24 connecting internal upstream containers 18 to downstream collector 46; and/or dispensing conduits 24 connecting one or more apparatus-1-external containers 16 to collector 46 via one or more inlets 38. Each single dispensing conduit 24 may be connected to a single container 18 via its upper end and to collector 46 via its lower end. The lower ends of all dispensing conduits 24 may be connected each one to a single dispensing valve 30. The plurality of dispensing valves 30 may be placed inside the collector 46, right on the top of balance plate(s) 44 as a packed monolayer of arrayed individual valves 30. Alternatively, dispensing 30 may consist in a single and compact multivalve selector/manifold 30 placed on the top of balance plates 44. The dispensing system may be automatically or manually controlled to connect select containers 18, 16 to the collector 46. In another embodiment, the dispensing system may be a simpler, conduit-free system, consisting in one or more large shallow dispensing collectors 46 placed underneath a set of storage containers 18 or all containers 18. The collector 46 may have a central position common to all downstream PCs 54. In this setting, the collector 46 may be connected to downstream PCs 54 through a radial array of flexible dispensing conduits each one connected to a PC 54. Otherwise, PCs 54 can be animated to move/slide underneath the common central collector 46 to retrieve dosed raw materials. Alternatively, the dispensing collector 46, can be animated to travel between downstream PCs 54 positions, alone or along with corresponding ingredient library 10.

The raw material conditioning units 40 are the devices that may allow each screening line to condition raw materials through heating or cooling (to the desired temperature), degassing or making ingredient gradients. The conditioning units 40 may be placed immediately downstream of storage containers 16, 18 in order for raw materials to be conditioned before their processing. In other cases, conditioning devices 40, namely heating or cooling, may be placed in raw material storage containers 14 in order to respect regulations, to prevent raw material alteration or simply to provide the screening line 8 with a ready-to-use source of hot or cold raw material as it may be required by a given formulation. Conditioned storage is also ideal for regular traffic of high density materials e.g., solvents like glycerol or nutrients like honey and syrups.

The dosing system is the device that may be used by each screening line 8 to measure the amounts of raw materials to be used in a formulation. The dosing system may mobilize a flow-based mechanism or a weight-based mechanism or a combination thereof. The flow-based mechanism is configured to measure the flow of materials while they are liberated from the storage source 18 16 through the dispensing valves 30. This mechanism presents the advantage of saving time because it may dispense simultaneously all raw material of a given ingredient combination but it suffers from the need of regular calibrations. The weight-based mechanism may mobilize balance plate (s) 44 configured to measure the weight of raw materials. The balance plate 44 is installed in the collector 46 underneath the valves 30. Balance plates 44 are also capable of serial dosing consisting in weighing several raw material in tandem, one after the other (cumulative dosing), before transferring them as one piece to downstream compartments. This mechanism also presents time saving because it does not require washing the balance plate between dosing sequences of an ingredient combination. The uncontested advantage of balance-based dosing is the capacity of weighing viscous ingredients (e.g., glycerol). Alternatively, the weight-based mechanism may mobilize load cells 20 connected with, and configured to measure the weight of containers 18, 16 or material exits from the containers 18, 16. Load cell-based dosing mechanism also presents the advantage of saving time because it may dispense simultaneously all ingredients of a given combination without the need for calibration. The flow-based and/or balance-based dosing mechanisms may be optional when the load cell-based mechanism is operational, and vice versa. Alternatively, the three dosing mechanisms may be installed together in order to complement each other and offer ultra-high precision and calibration-free dosing mechanism, that is required for highly regulated settings.

The collector 46 is the element that may be used by each screening line 8 to pool and combine dosed materials (target entity and secondary ingredients). It lies between the dosing system and downstream PC 54 in the compartment 3. Given its central position and its funnel shaped bottom, collector 46 also serve to convey dry or wet ingredient combinations to downstream formulation compartment PC 54 and then FC 66.

The active transfer is the mechanism that may allow each screening line 8 to convey dosed ingredient combinations from collector 46 to downstream compartments. The active transfer mechanism comprises nozzles 48 that are configured to spray cold or hot liquid solvents. These solvent sprays may suspend and dissolve ingredient combinations into crude liquid premixes and then transfer them to downstream compartments 4 and 5. Alternatively, the transfer may be performed by mild compressed air, vacuum or both (dry transfer) to evacuate collector 46. In settings using balance-based dosing, wet transfer using nozzles 48 may be preferable and can be set to perform vigorous and/or hot solvent sprays capable of washing weighed ingredients (including viscous solvents) efficiently out of the balance plate 44 and collector 46 walls. In a balance-free system, dry transfer may be preferable. However, in balance-free systems, nozzles 48 may be set to feed collector 46 with very weak but continuous solvent stream capable of forming a solvent microfilm throughout collector 46 walls. This novel mechanism may serve in immediate capture and transfer of extra light, fluffy and volatile materials while they are dispensed from container 18.

Each screening line 8 may also comprise three types of formulation chambers preferably disposed vertically one above the other. at least two pre-formulation chambers (PCs) 54 adapted to receive the ingredient combinations from the collector 46 and make pre-mixes, working solutions, or stock solutions; a central formulation chamber (FC) 66 adapted to receive the pre-mixes, working solutions, stock solutions and combination thereof and adjust/complete such pre-mixes to produce a final formulation, and a lateral stress chamber (SC) 80 adapted to subject forming or final formulations to stress treatments. The PCs 54 are installed in the compartment 4 whereas the FC 66 and the SC 80 are installed in the compartment 5.

As a consequence of the possible aforementioned high throughput, multiplicity of screening lines, apparatus 1 may be configured to hold a large number of formulation chambers. This should allow apparatus 1 to formulate and test large numbers of target entities and secondary ingredients in a relatively short time. This should reduce the duration of development of new formulations and increase the launch of new entities to market. The capacity of formulation chambers may range from 1 ml or less in ultra-HTS stations involving several hundred (500 or more) screening lines 8; to 10 ml or 50 ml in special HTS setting involving a few hundred (100-200) screening lines 8. In limited throughputs, involving 100, 50 or less screening lines 8, chamber capacity may reach 100 ml, 250 ml, 500 ml, 1000 ml or more. Formulation chambers PCs 54, FCs 66 and SC 80 may be animated to travel individually or as compact plates of multi-PCs 54, multi-FCs 66 or multi-SCs 80 to reach a common upstream collector or collectors 46 in order to retrieve prepared premixes. Furthermore, plates of formulation chambers multi-FCs 66 and multi-SC 80 may be disposable, i.e., completely detachable from apparatus 1 either manually or using a robotic arm (like those used by HTS reading stations) dedicated to place them directly in one of tandem devices 94 or any multi reading station.

Mobility of formulation chambers is ideal for quick straightforward reading/monitoring (screening of formulations) in FC 66 either manually or by relevant apparatus-1-dependent (94) or independent devices such as plate readers. Mobility of chambers may also be required for controlled long term incubations of SC 80 for stability studies and the like and therefore leaving room in the device for subsequent time points of the same screening run or for independent new runs. Mobility of formulation chambers may allow user to save time spent by apparatus 1 in long GLP, GMP, GCP-compliance demanding cleaning cycles since removed chambers 66 and 80 may be replaced readily by new freshly unpacked, clean and sterile multi-chambers plates, either manually or using robotic arm.

Each screening line may comprise a series of sensors including load cells 20, 44, and other probes 60, 72, 86 that can be thermometers, volume detectors, pH meters, nephelometers, particle counters, viscosimeters, optical density (visible or UV), cameras and the like. These sensors are fundamental to the screening activity of apparatus 1 because they allow it to compare between formulations in order to pick the right target compound, the right secondary ingredients, the right formulation protocols or other combinations.

a) Screening for target entities consists in comparing between different entities for properties like solubility, stability, function/activity or many other physical and chemical properties.

b) Screening for secondary ingredients consist in testing a large panoply of ingredients or ingredient combinations in order to pick one or a handful that improve one or several properties of a target entity. For instance screening a library of preservatives in order to select the one preservative that confers the highest stability of a food preparation or a new beverage in hot environments.

c) Screening for formulation protocols, means that apparatus 1 can formulate a target entity in a dozen different protocols (for instance) and finally selects the one that allows for quick and sustained dissolution (solubility) of a chemical.

Each screening line 8 may comprise a series of actuators that may include pumps, 34, 50, 62, 76, 90, valves, 30, switch valves 36, 52, 78; spraying nozzles 48, 56, 58 and 82; stirrers/homogenizers 58, 70; 84, heating/cooling systems, visible/UV light devices 74, 88; injectors 64; auto samplers 96; carousel 98; hot air conveyor 108.

The mentioned actuators allow to each screening line 8 to handle, manage and process raw materials and final formulations as follows. dispensing/dosing of raw materials; suspension of ingredient combinations; traffic of ingredient combinations and final formulation between compartments and to exit points; conditioning of raw materials and final formulations; formulation of ingredient combination; stress treatments; discharge of formulations and cleaning of chambers and connecting conduits.

Solution conditioning devices 92 may be used in the preparation of forming or finished formulations for special detection assays and methods that can't be monitored by regular sensors placed in FC 66 or SC 80. The devices 92 may consist in a degassing unit, a decanting unit, an ultrafiltration unit, a connection to speed-vacuum/freeze-drying/lyophilization unit, or a combination thereof. The devices 92 are installed in the compartment 5 or in the same compartment as the FC 66 and the SC 80.

Each screening line 8 may also comprise one or more injectors 64 adapted to administer additional raw or processed materials into the PC 54, FC 66 or SC 80 for combination with a premix or a forming formulation and an auto-sampler 96 adapted to draw out a portion of forming or final formulation at different or fixed time points during the formulation or screening process. Samples drawn out by the sampler 96 may be monitored by the external devices 94, stored for long term studies or used in related assays. A carousel 98 or any similar device known in the art, for holding a plurality of sampling vessels 102. And a terminal waste lines 100 per screening line, or multiple compartment-dedicated waste lines, one for each formulation chambers (collector 46, PCs 54, FC 66, SC 80) adapted to evacuate corresponding chambers during screening runs or the whole apparatus 1 between runs (during the cleaning cycle). The devices 94 are preferably external to the apparatus 1 and may include a high performance liquid chromatography (HPLC) system, a liquid chromatography-mass spectrometry (LC/MS) system, an SPR system (Biacore) system, a plate reader, a nuclear magnetic resonance spectroscopy (NMR) system or other analytic devices. The devices 94 may mobilize a common articulated robotic arm that is dedicated to the automatic withdrawal of multi-chamber plates and vessels (66, 80, 102) from apparatus 1 and their relocation to one or the other or connected tandem devices 94. Optionally, the devices 94 may be arranged inside the apparatus 1. The external device 94 and its activities (operations and generated data) are connected with apparatus 1 under the control of computer 104.

The vessels 102 may be regular or sterile test tubes, micro-well plates, vials, flasks, petri-dishes, bottles and the like and are arranged in the compartment 6. The vessels 102 may be empty or pre-filled with inert solutions and/or buffers alone or supplemented with components relevant to subsequent assays. As it is the case with multi-chamber plates 66 and 80, vessels 102 may also be withdrawn from apparatus 1 either manually or using a robotic arm dedicated to place them directly in one of tandem devices 94 or any multi reading station.

The computer 104 serves as an interface between the user and the apparatus 1 and is used to control the latter. The computer 104 may comprise a processor, a memory (which may be transient, non-transient or a combination thereof) for storing a high throughput screening (HTS) module having computer instructions and storing acquired screening data, and a database for storing target entities and secondary ingredients information. The computer instructions are executable by the processor. When computer instructions are executed by the processor, they causes the processor to instruct the apparatus 1 to perform the formulation, screening, and the analysis of the screening outcome and data, as well as the steps described above. The data generated from all those steps may also be stored in the memory, in addition to the acquired screening data.

A method for developing new formulations through the HTS screening of ingredient combinations using the system 100 is also contemplated. In one embodiment, the method may comprise receiving orders from a user through the computer 104, preparing combinations of target entities with secondary ingredients according to the user's orders, formulating the multiple combinations to produce multiple final formulations, applying stress treatments to the formulations, while monitoring and comparing between the formulations (screening), and then transferring samples of the formulations to tandem devices or delivering them into external vessels for further studies. All the aforementioned steps are performed by apparatus 1 and dependent external devices and may be reported by computer 104 in real time or as print reports. At the end of the screening program, the method may further comprise a cleaning step that cleans the apparatus 1.

Real time refers to a process in which the outcome of the process occurs or is generated at what appears to be (to the user or observer) at the same time or nearly the same time as inputs for the process are received or occur.

In a pharmaceutical setting for instance, upon receiving target compounds (e.g., drug candidates, hits or lead compounds), the user integrates the compounds in apparatus 1 either through the storage in the relevant containers 18, 16 or by injection through injector 64. The user then places an order on the computer 104 requesting the apparatus 1 to run a screening. The screening program may be automatic or manual. In automatic screening mode, the computer 104 fully controls the apparatus 1, injector 64 and/or external devices 94, selects and executes screening parameters and settings. In manual screening mode, the user enters the desired parameters and settings. These parameters and settings may include the properties of the target compound to be monitored, target values to be met for each property, libraries to be screened to meet these properties as well as screening mode (e.g., targeted, random etc.) to be performed and the like.

Once an order has been placed, the computer 104 gives instructions to a set or all screening lines 8 of apparatus 1 to produce formulate, stress and then screen different ingredient combinations. This will prompts the dispensing and dosing systems 24, 30, 44 of activated screening lines 8 to launch a powerful program of "combinatorial formulation" consisting in high speed parallel differential dosing of raw materials capable of preparing simultaneously large numbers of complex ingredient combinations in a short time.

These combinations may involve fixed or variable target compound plus discrete, extreme or intermediate variations of second ingredients. For example, these combinations may be:

a) Te+(A1 B1 C1 D1), Te+(A1 B1 C1 D2), Te+(A1 B1 C1 D3), Te+(A1 B1 C1 D4)
b) Te+(A1 B1 C1 D1), Te+(A10 B6 C3 D9), Te+(A5 B12 C8 D13), Te+(A2 B18 C5 D1) Wherein "Te" is the target entity and the remaining four alphabets represent a combination of four different second ingredients from four libraries: A: a library of antimicrobials; B: a library of buffers; C: a library of stabilizers and D: a library of solubilizer. The numbers are the different ingredients of this same library as in A1: a first antmicrobial of the library, A2: a second, different antimicrobial of this library and so on.

The dosed ingredient combination in each screening line 8 is pooled in the collector 46 into a crude premix and then transferred to PC 54 using solvent spray from nozzles 48, air pressure, vacuum, pump 50 or a combination thereof. The crude premix may be transferred directly to FC 66 using pump 62. In the second PC 54, the premix is transformed into a finished working or stock solution by the adjustment of its volume, its concentration, homogeneity and pH using nozzles 56, stirrers 58 and heating 88. Working or stock solutions may be prepared by a screening line 8 to serve in progressive titration of previously transferred crude premix (in FC 66) with a target entity, a given secondary ingredient or a combination thereof; or in order to make single or serial dilutions of the mentioned ingredients.

Following their transfer to FC 66, the crude premix in each screening line 8 is adjusted to a minimum formulation volume and starts to be monitored for properties like, dissolution, viscosity, pH, some target entity's activity (made possible by some fluorescent or labeled probes in the combination) and the like using FC 66 inline sensors including optical OD sensors 72. In the same time, computer 104 attempts to push the formulation to target property(s) dictated by the user. This may include meeting a set pH value, reaching full dissolution and homogeneity of the formulation and/or lowering the formulation's viscosity. This may be accomplished through vigorous stirring, heating, cooling, dilutions/concentration, pH adjustment or combinations thereof using respective actuators (feeding pump 62, spray nozzle 68, stirrers 70 and heating/cooling actuators 74).

During the adjustment and monitoring of formulations, using relevant actuators and detectors, computer 104, alone or under the control of the user, may highlight, on computer's screen display 104, the screening line(s) 8 holding hit formulation(s) i.e., the formulations with successful ingredient combinations that have partially or completely met expected properties of target compound (s).

While unsuccessful formulations may be aborted or retained for further improvements, samples of hit formulations may be transferred to SC 80 to undergo forced stability studies. This consists in applying a stronger, than normal, but acute doses of stress to the formulation in order to determine whether this formulation is capable to confer protection of target entity against stress-induced precipitation, degradation or loss of activity under. The applied stress treatment can be chemical or physical or a combination thereof and may be induced by actuators such as feeding pumps 62, 76, nozzles 68, 82 capable of injecting strong acids and bases; or by visible and UV light and other devices 74, 88 capable of providing intense light, excessive heat, repeated freezing/thawing cycles or radiation and the like.

At the end of stress treatment, the hit formulation that succeeded to preserve target compound's properties under stress, may be subjected to further analysis following three extra monitoring paths, one tandem monitoring, and two different offline monitoring.

In the case of tandem monitoring, an aliquot of the hit formulation may be transferred to apparatus-1-connected devices 94 either directly using appropriate pumps 76 or after preparation by conditioning devices 92. Tandem devices 94 will allow user to confirm the stability of target entity using more accurate and quantitative detection methods such as HPLC, LC-MS and/or NMR analyses capable of revealing possible stress induced alterations like degradation (hydrolysis or photolysis) of target entity oxidation, structural modification, or other combinations.

In a first offline monitoring mode, the hit formulation may be withdrawn completely out of apparatus 1 within its corresponding chamber SC 80 either manually or automatically using an articulated robotic arm 94. The hit formulation, and thus target entities, can be subjected to accelerated (3-6 months of stress) or long term stability studies (12 months or more of stress) without even leaving dedicated chambers SC 80. One advantage with this novel testing/monitoring method is the possibility for previously withdrawn samples to re-integrate the apparatus 1 at any time for further processing (formulation) or monitoring either by inline, tandem mode using devices 94.

In the second off-line monitoring mode, a portion of the hit formulation may be discharged through the auto sampler

96 into appropriate vessels 102. Then the vessels are withdrawn from apparatus 1 either manually or automatically using an articulated robotic arm 94. The discharged sample (s) of hit formulations may serve in one or more analyses rather focusing on target entity's functional activity. In fact these analyses allow the user to determine whether, the "in-line" hit formulation (that conferred solubility and/or stability to a target entity) has also protected the functional activity of the target entity from stress treatment.

Consequently, discharged samples of the hit formulation may have the possibility to be used in an infinite list of in vitro assays and in vivo studies in order to confirm the functionality of the target entity. Most of these studies are generally carried out on molecules such as target entity's ligands or substrates (biochemistry, molecular and enzymatic assays); target cell lines, cell extracts, or microorganisms (cell-based, immunological and microbiological assays); or in vivo studies may be performed on entire organisms (plants, animal models, pre-clinical and clinical studies). Presented below, a non-exhaustive selection of examples illustrating some cases of in vitro and in vivo studies. In one case, a discharged sample of hit formulation is incubated with a cell culture in order test whether the formulation preserved the cell killing activity (efficacy and stability) of the formulated target compound (drug candidate, a pesticide or an insecticide). This same assay may proof valuable for determining whether the formulation preserved the solubility of the tested drug in artificial or physiological media as well as its permeability into target cells required for its killing activity. This assay may mobilize a plate reader and/or flow cytometer.

In a second case, a discharged sample of hit formulation serves to inoculate a liquid or solid (agar) culture media in order to determine whether antimicrobial ingredient of the formulation protects target entity from microbial attacks even in non-sterile conditions. Or hit formulation sample can be used in infected culture media to determine if the formulation has preserved the antibiotic activity of a newly discovered small molecule entity.

In one embodiment, a discharged sample of hit formulation is incubated with a specific substrate of target entity in order to check whether the formulation preserved the binding activity of target compound to its molecular substrate. This assay may mobilize a colorimetric or radioactive detection method performed by a plate reader.

In another embodiments, a discharged sample of hit formulation is mixed with food preparations or beverages (e.g., milk or juice etc.) in order determine, via regular degustation or using analytical methods, whether formulation preserved the taste and/or the miscibility of the target entity (newly discovered or developed flavor, excipient, condiment etc.).

In another instance, a discharged sample of hit formulation is incubated with human or animal cell extracts (cell-free system) in order to determine which one of the screened formulations preserves the capacity of the target entity (a newly discovered drug) to bind its therapeutic cellular target.

In other embodiments, a discharged sample of hit formulation is subjected to DNA or protein electrophoretic separation or blotting methods in order to detect possible degradation of target entity (if protein or DNA) or interactions of the entity with other proteins.

In another embodiment, a sample from a hit formulation may be used as an experimental drug candidate to treat animal models (mice, monkeys, dogs etc.) plants or patients in pre-clinical and authorized clinical studies t) in order to determine parameters such as syringibility, of hit formulation, its safety to treated subjects; efficacy of target compound, toxicity.

In another embodiment, a sample from a hit formulation may be applied to a series of material (textile, electronic boards, walls etc.) in order to check whether the stabilizing formulation have not altered the coating and/or adherence activities of a new chemical The corresponding immediate, mid or long term data (in vitro, in vivo and stability) gathered from tandem and off-line monitoring may be integrated buy computer 104 along with previous primary screening data (formulation and forced stability screenings) to form a complete file on development and testing of target compound formulations.

At the end of each screening cycle, the computer 104 may launch a cleaning process comprising a wet cycle and a dry cycle. The wet cycle may comprise rinsing the apparatus 1 with cold or hot water or relevant cleaning solvents and detergents from top to bottom using nozzles and pumps placed along the screening line. The wet cycle may be followed by a dry cycle comprising pumping hot air into the apparatus 1 and circulating the pumped hot air through some or all of the compartments. The hot air may be generated by a hot air generator 108. In one embodiment, the hot air generator 108 may include a pump and associated hoses to pump hot air into the collector 46 (or compartment 3), the PCs 54 (or compartment 4) and the FC 66 and SC 80 (or compartment 5).

To perform all of the aforementioned steps, the computer 104 or the HTS module may be configured to perform multiple operations. The operations may comprise integrating orders input by users, managing and data mining information from libraries and scientific literatures, controlling screening processes by screening lines, analyzing, comparing and organizing data (or properties) obtained from the screening processes, reporting status of screening processes and the analyzed, compared and organized data in real-time, and saving the status of screening processes and the analyzed, compared and organized data. Information from libraries may be entered by the user and information from scientific literatures may be pre-stored in the computer 104, available on the web or a combination thereof.

Data obtained from the screening processes may be analyzed, compared or organized in groups defined by the user through the computer 104. The groups may comprise groups exhibiting poor properties to groups exhibiting superior properties and other user-defined groups. As such, the formulations in each group may be further screened according to the properties they manifest. Real-time reporting may include status of the screening process of each screening lines, time lapsed, the amount of kinetic energy involved in developing the formulation, formulation parameters (e.g., volume, temperature, pH, ingredient dose, turbidity, viscosity and the like). Real-time reporting allows the user to stay informed of the screening processes and make adjustments or intervene if needed, such as to correct deviations or abort a screening process. The reporting may be individualized for each screening process, a collective summary of some or all of the screening processes or a combination thereof. In individual reporting, it may include the formulation's behavior with respect each formulation parameter. The collective summary may be presented in a table, a spreadsheet or a matrix and may present raw or analyzed screening data. The collective summary may also rank or classify the formulations based on their exhibited properties. All these reporting may be saved for future analysis and studies and for checking if the user and the system 100 have complied with Good Laboratory Practice (GLP), Good Manufacturing Practice (GMP) and Good Clinical Practice (GCP).

In its activity of assuring the interface with user and controlling the apparatus 1, the computer 104 executes a plurality of interdependent operations necessary for the HTS-activity of the present technology:

1. Integration of screening orders from a user using a memory;

2. Management and data mining of information from ingredient database libraries 10 and/or internally stored or web-based literature;

3. Activation and control of screening operations executed by screening lines 8;

4. Analysis, using an installed screening application software, of data generated from different screening lines 8, their comparison and organization into separate groups, for example from bad to good, using criteria and cut-offs initially entered by the user in the screening software. This allows identification of good formulation(s) hits, comparison and classification prioritization of formulation(s) from the same screening set (intra), or from distinct screening sets (inter). This analytical/organizational ability endows the computer 104 with an automatic decision power, when the computer 104 can chose the direction of subsequent screening runs based on the outcome of previous ones.

5. Real-time reporting of the above activities as interactive on-screen displays is executed as follows. During screening runs, the computer 104 displays in real-time at least the following: progress of the screening process of all working screening lines, e.g., current operation, mode, status and evolution over time, kinetics, of all formulation parameters, e.g., volume, temperature, pH, ingredient dose, turbidity, viscosity simultaneously as progressing color-coded curves. This kind of display allows the user to stay informed on screening status and outcome and intervene if needed, at any moment either to adjust or correct deviations to plan, experiment ideas or simply abort running operations. At the end of screening runs, the computer 104 reports screening outcome either as individual data of single screening runs, or as pooled data summarizing results from several runs. Individual reporting mode is exhaustive and displays all the information corresponding to a screening run including screening data plots with formulation parameters curves along with screening process operations. It represents a finalized and complete version of the screening run display. However, pooled reporting mode focuses only on screening data that might be presented as tables, spreadsheets or matrix of plots from a whole screening set or campaign. The computer 104 can present pooled data as crude or analyzed screening data, wherein spreadsheets and matrix plots are organized and classified as gradients from bad to good formulations and/or highlighted or tagged hit formulations. More complex types of displays of analyzed data such as plot overlays, matrix of plot overlays, histograms and heatmaps or the like can also be provided by the computer 104. The user has the choice to print one or the other of the reporting modes described above for further analysis, studies, audits or simply for routine records pasted in laboratory note books.

6. Real-time recording, using memory of all the above operations. These records may serve in executing identical screening runs or campaigns in the future and answering troubleshooting inquiries or during internal/external Good Laboratory Practice (GLP), Good Manufacturing Practice (GMP) and Good Clinical Practice (GCP) auditing.

It should be understood that the term "may" is often time used to communicate that this is one embodiment and other variations are contemplated.

The present disclosure is further supplemented by the U.S. patent application Ser. No. 13/426,261, entitled "Automated High Precision Solution Preparation Apparatus" and filed on Mar. 21, 2012, the entirety of which is herein incorporated herein by reference.

Module in this disclosure refers to software module that is executed by the processor of the computer 104.

Counterpart method and computer-readable medium embodiments would be understood from the above and the overall disclosure. Counterpart method refers to the method performs by the system 100 and each of the components in the system 100 (e.g., the formulation development apparatus 1, the external devices 94, the computer 104 and the devices 94.). It would be understood that the method/processes/steps that are described to be controlled by computer operation can be stored on computer readable medium as computer readable instructions that carry out the steps of those methods/processes/steps.

Unless defined otherwise, all technical and scientific terms used herein have the same meaning as commonly understood by one of ordinary skill in the art to which this invention belongs. Although any methods and materials similar or equivalent to those described herein can also be used in the practice of the present invention, exemplary methods and materials are described for illustrative purposes. All publications mentioned in this application are incorporated by reference to disclose and describe the methods and/or materials in connection with which the publications are cited.

Additionally, the publications discussed herein are provided solely for their disclosure prior to the filing date of the present application. Nothing herein should be construed as an admission that the present invention is not entitled to antedate such publication by virtue of prior invention. Further, the dates of publication provided may be different from the actual publication dates, which may need to be independently confirmed.

Further since numerous modifications and changes will readily be apparent to those having ordinary skill in the art, it is not desired to limit the invention to the exact constructions as demonstrated in this disclosure. Accordingly, all suitable modifications and equivalents may be resorted to falling within the scope of the invention.

Thus for example any sequence(s) and/or temporal order of steps of various processes or methods or sequence of system connections or operation that are described herein are illustrative and should not be interpreted as being restrictive. Accordingly, it should be understood that although steps of various processes or methods or connections or sequence of operations may be shown and described as being in a sequence or temporal order, but they are not necessary limited to being carried out in any particular sequence or order. For example, the steps in such processes or methods generally may be carried out in various different sequences and orders, while still falling within the scope of the present invention. Although a specific system has been described, broader invention that would include some elements are also contemplated herein this disclosure.

Unless defined otherwise, all technical and scientific terms used herein this disclosure have same meaning as commonly understood by one of ordinary skill in the art to which this invention belongs. As used herein and in the appended claims, the singular form "a," "and," "the" include plural referents unless the context clearly dictates otherwise. All technical and scientific terms used herein have the same meaning.

Although the present invention has been described and illustrated herein with referred to preferred embodiments, it will be apparent to those of ordinary skill in the art that other embodiments may perform similar functions and/or achieve like results. Thus it should be understood that various features and aspects of the disclosed of the disclosed embodiments can be combined with, or substituted for one another in order to form varying modes of the disclosed invention. Many different embodiments such as variations, adaptations, modifications, and equivalent arrangements are will be implicitly and explicitly disclosed by the embodiments described herein, and thus fall within the scope and spirit of the present invention.

Thus, the scope of the embodiments of the present invention should be determined by the appended claims and their legal equivalents rather than by the FIGURE.

What is claimed is:

1. An automated system for developing new formulations of a target entity, the system comprising:
    an automated apparatus comprising:
        a plurality of screening lines, wherein each of the plurality of screening lines comprises:
        a plurality of upstream storage containers adapted to receive raw materials, wherein the raw materials comprise the target entity and secondary ingredients;
        at least one device that is adapted to condition before they are received in the storage containers, while they are in the storage containers, or after they exit the storage containers;
        a dispensing system comprising a central common collector and a plurality of conduits connected to each of the storage containers;
        a dosing system that measures amounts of the target entity and the secondary ingredients to be combined as an ingredient combination;
        a collector that pools the target entity and the secondary ingredients as the ingredient combination;
        a plurality of formulation chambers adapted to prepare formulations from the ingredient combination and perform stress treatment on the prepared formulations;
        a plurality of in-line sensors installed in the formulation chambers for monitoring properties of the ingredient combination and screening formulations of the ingredient combination;
        a plurality of actuators comprising pumps, valves, nozzles, and stirrers adapted to transfer raw materials and formulation between compartments and chambers;
        at least one injector that is adapted to administer additional target entity and secondary ingredients into one of the formulation chambers to be formulated with the ingredient combination in that formulation chamber;
        an auto-sampler for drawing out a portion of formulations prepared by the formulation chambers as samples or final formulated materials;
        at least one carousel for holding a plurality of vessels for containing the drawn samples or final formulated materials; and
        a waste line for evacuating waste out of the apparatus after a cleaning cycle;
    a plurality of analytical devices coupled to the apparatus that are controlled by a computer; and
    an articulated robotic arm connected to the apparatus and operated by the computer for automatically loading and unloading the formulation chambers and vessels between the apparatus and the analytical devices for analyses.

2. The system of claim 1, wherein the plurality of screening lines comprise 5 to 50 screening lines that are adapted to conduct high throughput screening or ultrahigh throughput screening of ingredients and formulations.

3. The system of claim 1, wherein the apparatus is adapted to handle a chemical or a biological molecule including a nucleic acid, protein, antibody, peptide, pharmaceutical, biological drug, medicine, diagnostic reagent, cosmetic, nutrient, chemical reagent, polymer, nanostructure or a combination thereof.

4. The system of claim 1, wherein the apparatus is adapted to handle a pharmaceutical, a chemical or a food ingredient including liquids, solvents, solids, vehicles, oils, buffers, solubilizers, surfactants, stabilizers, antimicrobials, preservatives, sweeteners, flavors, dyes, additives, excipients or a combination thereof.

5. The system of claim 1, wherein the apparatus is adapted to categorize the raw materials in storage containers as separate libraries, wherein one or more libraries are dedicated to target entities and multiple libraries are dedicated to secondary ingredients.

6. The system of claim 1, wherein one of the prepared formulations is cold or radioactive solution, a chemical or biological medicine, a diagnostic reagent, a cosmetic/fragrance, an agrochemical, a coating solution, a food recipe or a processed food preparation or a combination thereof.

7. The system of claim 1, wherein the conditioning of raw materials comprises degassing, heating, cooling or making a gradient of materials or a combination thereof.

8. The system of claim 1, wherein the central common collector is adapted to perform high speed parallel dispensing and the plurality of conduits are flexible conduits configured to perform high precision dispensing and dosing.

9. The system of claim 1, wherein the dosing system comprises a mechanism configured to measure weight of the target entity and secondary ingredients and a mechanism configured to measure flow rate of the target entity and secondary ingredients.

10. The system of claim 9, wherein the mechanism configured to measure weight of the target entity and secondary ingredients comprise load cells installed on the storage containers.

11. The system of claim 1, wherein the plurality of actuators further comprise heating and cooling devices, homogenizers, UV and visible light sources or a combination of thereof that are configured to process the raw materials, adjust formulations, and introduce acute stress into formulations.

12. The system of claim 1, wherein the plurality of sensors comprise a thermometer, a volume detector, a pH-meter, a nephelometer, a viscosimeter, a particle counter, a camera or a combination thereof.

13. The system of claim 1, wherein the analytical devices comprise at least a plate reader, a HPLC, a LC/MS, a NMR, a SPR/Biacore, or a combination thereof that is used to complement the monitoring and screening activities of the in-line sensors.

14. The system of claim 1, wherein the formulation chambers include single multi-FC and multi-SC plates that may be loaded or unloaded from the apparatus manually or automatically using the robotic arm for long term external incubations followed by reloading to the apparatus or for disposal and replacement by new unpacked sterile plates.

15. A method for developing new formulations of a target entity, the method comprising:
   receiving the target entity to be formulated;
   conditioning the received target entity;
   combining the target entity with secondary ingredients to produce an ingredient combination;
   formulating the ingredient combination to produce formulations;
   subjecting the formulations to a stress treatment;
   screening the formulations for the target entity's physical, chemical and functional properties;
   delivering a portion of the formulations as samples or final formulations to a plurality of vessels; and
   analyzing and comparing screening data from screening lines for finding hit formulations.

16. The method of claim 15, wherein the preparation of ingredient combination is based on a mechanism of high speed combinatorial formulation consisting in preparing multiple separate ingredient combinations at once in a short time, through the simultaneous execution of parallel ingredient dispensing in each screening line and differential ingredient dispensing between different screening lines.

17. The method of claim 15, wherein the step of screening comprises at least three screening types, and the at least three screening types comprise formulation screening involving in-line monitoring of the target entity's properties, stability screening involving in-line and tandem monitoring of the target entity's alteration under stress, and functional screening involving off-line monitoring of the target entity's functional activities.

18. The method of claim 15, wherein the stress treatment comprises chemical stress, physical stress or a combination thereof that can be executed in-line in stress chambers for short term forced stability studies and be performed outside the apparatus for long term stability studies.

19. The method of claim 15, wherein the step of analyzing and comparing comprises comparing all produced formulations utilizing a computer and a plurality of analytic devices.

20. A computer comprising a processor, a non-transient memory coupled to the processor, a set of computer instructions contained in the non-transient memory that are executable by the processor, the set of computer instructions when executed by the processor causes the processor to instruct an automated system for developing new formulations of a target entity comprising an automated apparatus, a plurality of analytic devices, and an articulated robotic arm to perform the steps of:
   conditioning the target entity and secondary ingredients received in the apparatus;
   dispensing the target entity and secondary ingredients through a dispensing system of the apparatus comprising a central common collector and a plurality of conduits, the target entity and secondary ingredients are dispensed to the central common collector via the plurality of conduits;
   measuring amounts of the target entity and the secondary ingredient to be combined as an ingredient combination;
   pooling the target entity and the secondary ingredients as the ingredient combination;
   preparing formulations from the ingredient combination and performing stress treatment in a plurality of formulation chambers of the apparatus;
   monitoring properties of the ingredient combination and screening formulations of the ingredient combination through a plurality of in-line sensors installed in the formulation chambers;
   transferring the target entity and the secondary ingredients between compartments and chambers of the apparatus via a plurality of actuators comprising pumps, valves, nozzles, and stirrers;
   administering additional target entity and secondary ingredients into one of the formulation chambers to be formulated with the ingredient combination in that formulation chamber from an injector;
   drawing out a portion of formulations prepared by the formulation chambers as samples or final formulated materials to a carousel for holding a plurality of vessels for containing the drawn samples or final formulated materials;
   instructing the analytical devices to screen the prepared formulations and find hit formulations; and
   operating the robotic arm to load and unload the formulation chambers and vessels between the apparatus and the analytics devices for analysis.

* * * * *